US00PP37275P3

(12) United States Plant Patent
Tan

(10) Patent No.: US PP37,275 P3
(45) Date of Patent: Feb. 17, 2026

(54) ***HIBISCUS* PLANT NAMED 'TAHI2025'**

(50) Latin Name: ***Hibiscus* x *moscheutos***
Varietal Denomination: Tahi2025

(71) Applicant: Alain Tan, Montauban (FR)

(72) Inventor: Alain Tan, Montauban (FR)

( * ) Notice: Subject to any disclaimer, the term of this patent is extended or adjusted under 35 U.S.C. 154(b) by 0 days.

(21) Appl. No.: 19/087,571

(22) Filed: Mar. 23, 2025

(65) Prior Publication Data

US 2026/0013409 P1 Jan. 8, 2026

(30) Foreign Application Priority Data

Jul. 2, 2024 (QZ) ..... PBR20241514

(51) Int. Cl.
*A01H 5/02* (2018.01)

(52) U.S. Cl.
USPC ..... Plt./257

(58) Field of Classification Search
USPC ..... Plt./257
CPC ... A01H 5/02; A01H 5/12; A01H 5/00; A01H 6/608; A01H 6/60
See application file for complete search history.

(56) References Cited

PUBLICATIONS

Facebook Canford Magna Garden Centre's Post 2024, retrieved on May 29, 2025 at https://www.facebook.com/story.php/?story_fbid=1000420728754027&id=100063583270154, one page. (Year: 2024).*
Facebook Peter Plantipp's Post 2024, retrieved on May 29, 2025 at https://www.facebook.com/peterplantipp/posts/hibiscus-carousel-ghost-looks-stunning-at-about-plants-zundert-bv-once-grown-car/1032048718748296/, one page. (Year: 2024).*
FloraXchange Hibiscus Carousel Ghost, retrieved on May 29, 2025 at https://www.floraxchange.nl/Artikel/Info/2285148/Hibiscus-Carousel-Ghost-(Tahi2025PBR), 2 pp. (Year: 2025).*
Instagram Pepiniere Fleurs du Sud 2023 retrieved on May 29, 2025 at https://www.instagram.com/p/CxL1R09IOqb/?hl=en, 3 pp. (Year: 2023).*

* cited by examiner

*Primary Examiner* — June Hwu
(74) *Attorney, Agent, or Firm* — Penny J. Aguirre

(57) ABSTRACT

A new cultivar of *Hibiscus* plant named 'Tahi2025' that is characterized by its upright, well-branched plant habit, its large flowers that are pure white in color, its leaves that are deeply incised, and its foliage with coloration that is green and flushed with red and purple in spring and becoming more purple and darker purple in summer.

3 Drawing Sheets

Botanical classification: *Hibiscus* x *moscheutos*.
Cultivar designation: 'Tahi2025'.

CROSS-REFERENCE TO RELATED APPLICATIONS

This application claims priority to European Community Plant Variety Office (CPVO) Plant Breeder's Rights Application No. 2024/1514 filed on Jul. 2, 2024, under 35 U.S.C. 119(f), the entire contents of which is incorporated by reference herein. The information for the plant breeders' rights application was received directly from the Inventor. This application is also related to U.S. Plant Patents derived from the same breeding program entitled *Hibiscus* Plant Named 'TAHI16' (U.S. Plant Pat. No. 28,282) and *Hibiscus* Plant Named 'TAHI56' (U.S. Plant Pat. No. 28,410).

BACKGROUND OF THE INVENTION

The present invention relates to a new and distinct cultivar of *Hibiscus* plant botanically known as *Hibiscus* x *moscheutos* 'Tahi2025' and will be referred to hereafter by its cultivar name, 'Tahi2025'. 'Tahi2025' is a new cultivar of hardy *Hibiscus* grown for use as a container and landscape plant.

The new cultivar was developed through an on-going breeding program conducted by the Inventor in Saint Martial, Montauban, France. The goal of the breeding program was to select a new cultivar of *Hibiscus* with a unique flower color in his proprietary series of *Hibiscus*. The new cultivar arose from open-pollination of numerous (both named and unnamed) plants in the Inventor's breeding program over many growing seasons. The Inventor pooled the collected seeds and therefore no specific parents are known. The Inventor selected 'Tahi2025' in July of 2020 as a single unique plant amongst the seedlings that resulted from the seeds sown.

Asexual propagation of the new cultivar was first accomplished by softwood stem cuttings in Montauban, France in August of 2020 by the Inventor. Asexual propagation by softwood stem cuttings and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'Tahi2025' as a new and distinct cultivar of *Hibiscus*.

1. 'Tahi2025' exhibits an upright, well-branched plant habit.

2. 'Tahi2025' exhibits large flowers that are pure white in color.
3. 'Tahi2025' exhibits leaves that are deeply incised.
4. 'Tahi2025' exhibits foliage with coloration that is green and flushed with red and purple in spring and becoming more purple and darker purple in summer.

'Tahi2025' can be compared to *Hibiscus* cultivars 'Kopper King' (U.S. Plant Pat. No. 10,793), 'TAHI16' (U.S. Plant Pat. No. 28,282) and 'TAHI56' (U.S. Plant Pat. No. 28,410). 'Kopper King' is similar to 'Tahi2025' in having burgundy leaves and flowers with white petals. 'Kopper King' differs from 'Tahi2025' in having a taller plant height, a less compact plant habit and flowers that are white with red centers. 'TAHI16' differs from 'Tahi2025' in having red flowers. 'TAHI56' differs from 'Tahi2025' in having flowers that are very pale purple-white in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantipp, Visions Pictures, Globe Planter, Ardcarne Garden Center, Botanico, Vitro Westland, Planterium/Groen Direkt, Safro Milan Havlis, RHS Plants, The Garden Society (Instagram), FlorAccess, Peter Plantipp (facebook and Youtube), Crocus, Floraria Secret Garden, Rose Barni, Primrose, Balcone Fiorito, Globe Planter, Promesse de fleurs, Gamm vert, FloraXchange, Donnadipiante, Megyeri Szabolcs, Zsohár Kertészet, FloraPris, Pépinière Fleurs de Sud, Concours Innovert, and Pépinière Laforet.

BRIEF DESCRIPTION OF THE DRAWINGS

The accompanying color photographs illustrate the overall appearance and distinct characteristics of the new *Hibiscus*. The photographs were taken of a plant 2 years in age of 'Tahi2025' as grown outdoors in a 23-cm container in Zundert, Netherlands.

The photograph in FIG. 1 provides a side view of 'Tahi2025' in spring.

Figure 1:
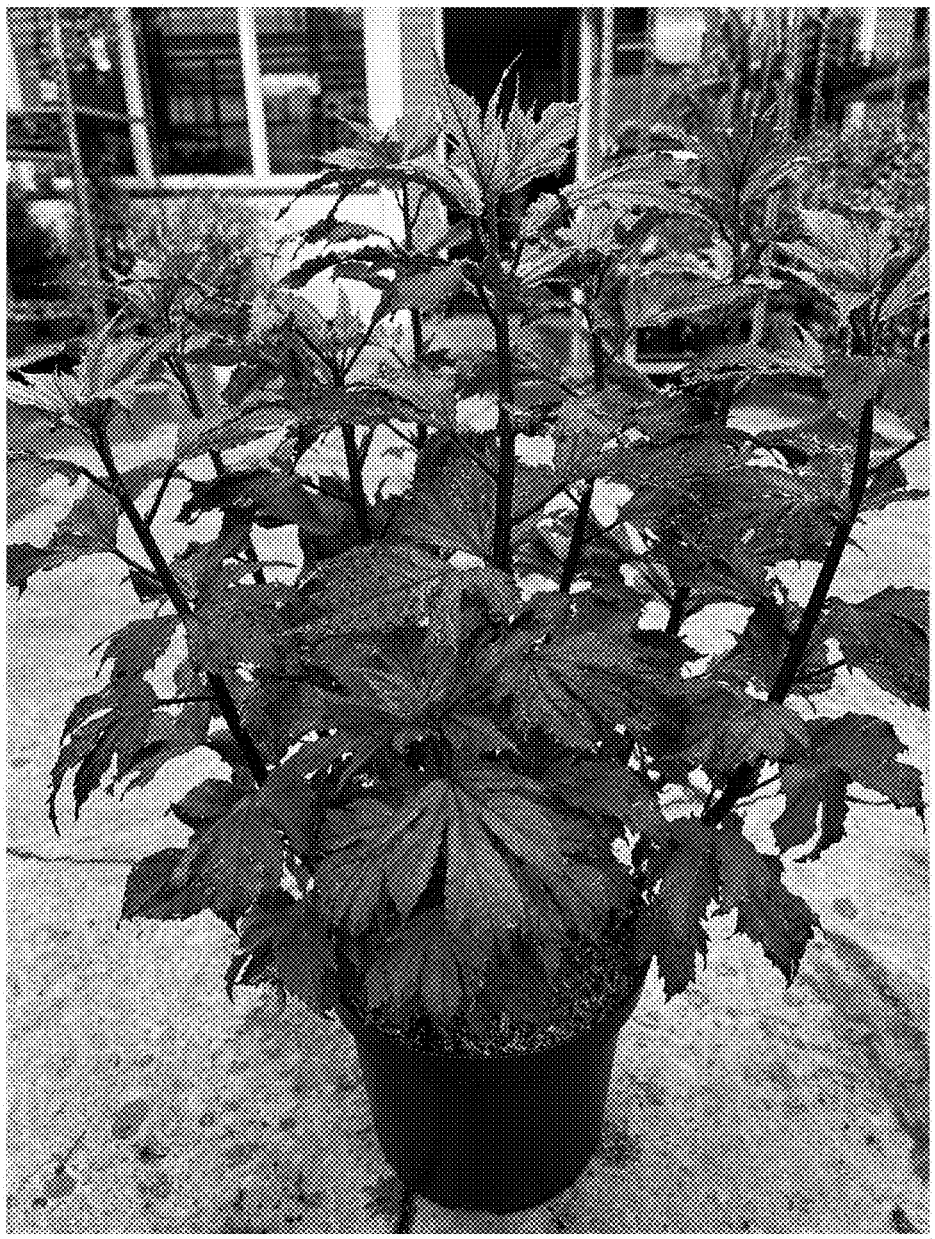
Figure 2:
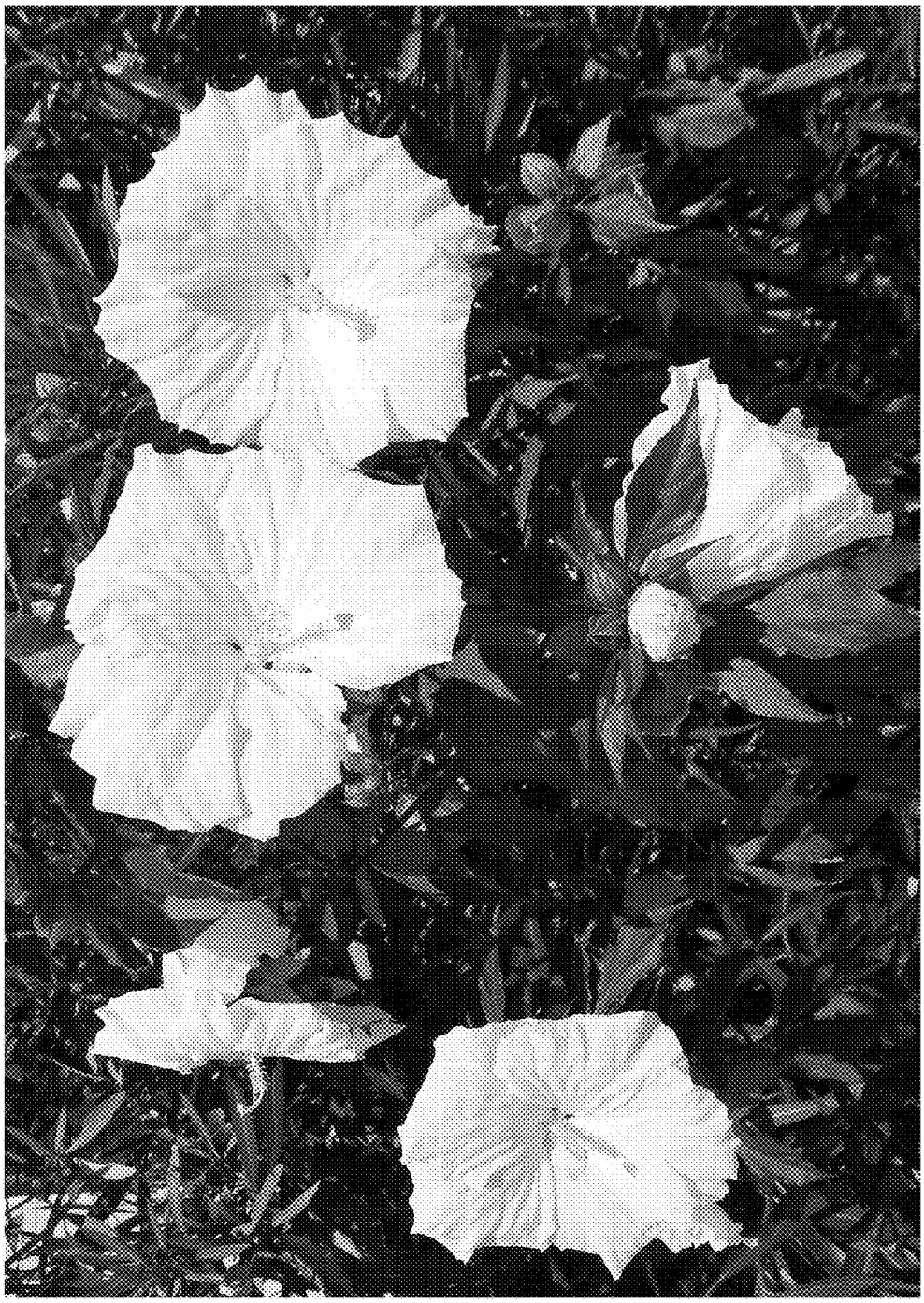

The photograph in FIG. 2 provides a close-up view of the flowers of 'Tahi2025'.

Figure 3:
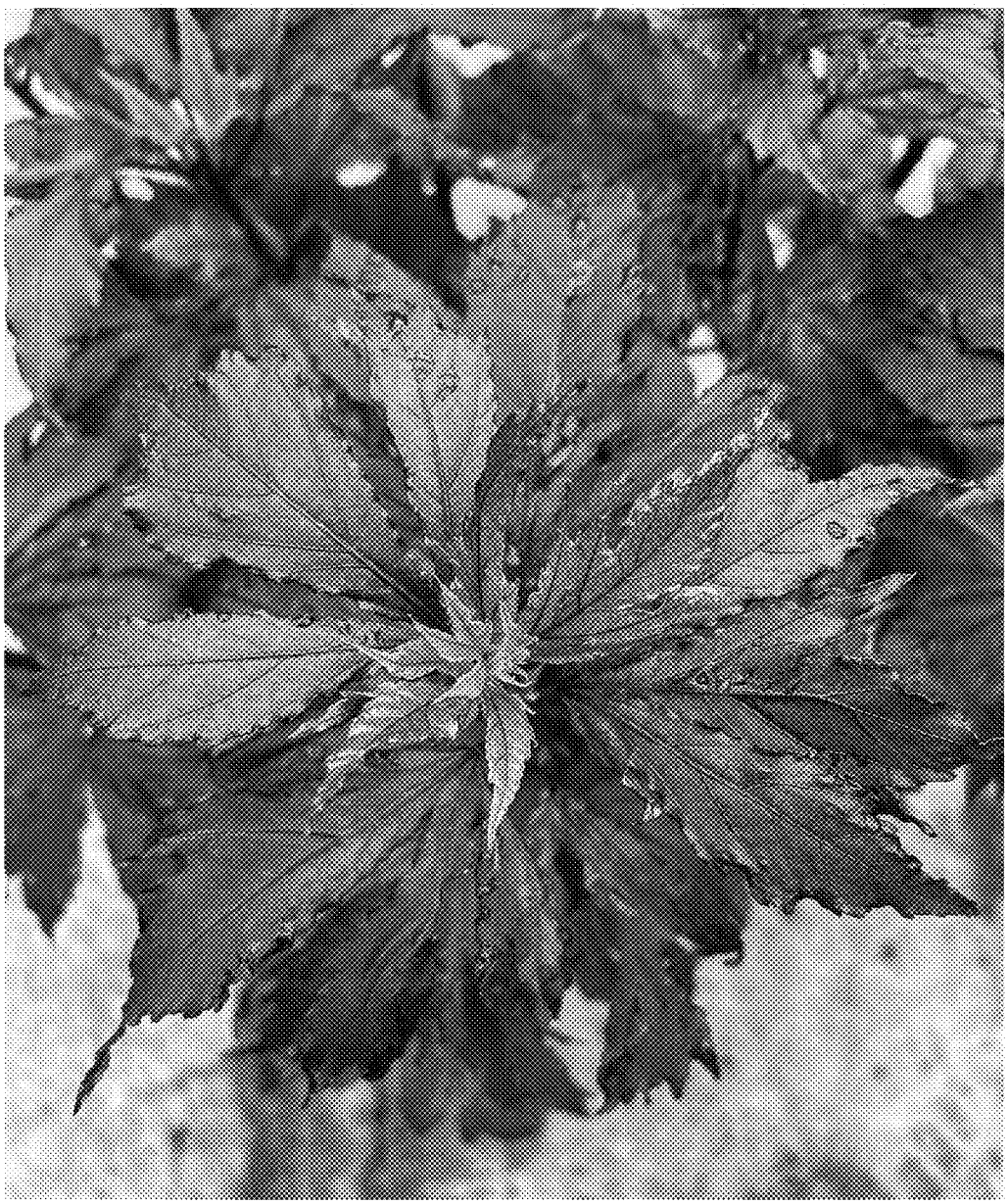

The photograph in FIG. 3 provides a close-up view of the foliage of 'Tahi2025' in summer.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 2-year-old plants of the new cultivar as grown outdoors in 23-cm container in Zundert, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period*.—Late summer to beginning of Autumn in France.

*Plant type*.—Herbaceous perennial.

*Plant habit*.—Upright, well-branched.

*Height and spread*.—Average of 95 cm in height and 78 cm in width as a 2 year-old plant grown in a container, reaches an average of 1.2 m in height and width as grown in the landscape.

*Cold hardiness*.—At least in U.S.D.A. Zone 5.

*Diseases and pests*.—No susceptibility or resistance to diseases or pests has been observed.

*Root description*.—Fibrous.

*Root development*.—Roots initiate in about 2 weeks and fully rooted young plant is produced in about 3 months.

*Propagation*.—Softwood stem cuttings and tissue culture.

*Growth rate*.—Moderately vigorous.

Stem description:

*Shape*.—Round.

*Stem color*.—144B, flushed with 178A to 178B.

*Stem size*.—An average of 86 cm in length and 2 cm in diameter.

*Stem surface*.—Glabrous.

*Stem aspect*.—Upright, in an average angle of 45° (0°=vertical).

*Stem strength*.—Strong.

*Branching*.—Moderately free branching, an average of 8 basal branches.

*Internode*.—Up to 4 cm.

Foliage description:

*Leaf shape*.—Hastate to narrow ovate.

*Leaf division*.—Simple.

*Leaf base*.—Hastate to truncate.

*Leaf apex*.—Long acuminate.

*Leaf venation*.—Pinnate, upper surface color; 183A, mid-rib 187B, lower surface color; 144C to 144D.

*Leaf margins*.—Deeply incised with lobes irregularly crenate to serrate, incisions medium in number, undulation medium.

*Leaf attachment*.—Petiolate.

*Leaf arrangement*.—Alternate.

*Leaf orientation*.—Held slightly pendulant.

*Leaf surface*.—Both surfaces glabrous, lower surface; very slightly pubescent.

*Leaf color*.—Young leaves upper surface; 143B with veins 183A, young leaves lower surface; 144B, tinged 183A and 200A, mature leaves upper surface; 144A and a blend of 200B and 183A along the veins and towards the tips, margins 183A, turns to a blend of 178A and N172A with irregular markings of N144A from the center to the base, then changes to 183A, mature leaves lower surface; 144B to 144D.

*Leaf size*.—Average of 12.5 cm in length, and 13 cm in width.

*Leaf quantity*.—Average of 23 leaves per lateral branch.

*Petioles*.—Average of 2.5 cm in length, 4 mm in width, upper surface color; slightly darker and than 183A in color, lower surface color; upper surface 187A, lower surface 144C to 144D, surface glabrous.

Flower description:

*Inflorescence type*.—Flowers are solitary in leaf axils.

*Lastingness of flowers*.—Average of 4 days, self cleaning.

*Flower size*.—An average of 5 cm in depth and 16 cm in diameter.

*Flower fragrance*.—None.

*Flower shape*.—Rotate, typical *Hibiscus* shape.

*Flower number*.—Average of 1 per lateral stem.

*Flower aspect*.—Outward to slightly upright.

*Flower bud*.—Ovate in shape, an average of 2.3 cm in length and 3 cm in diameter, color; 144A, flushed with 183A, surface glabrous.

*Flower attachment*.—Pedunculate.

*Petal number*.—5.

*Petal shape*.—Ovate.

*Petal color*.—Upper and lower surface when opening and fully open; NN155A.

*Petal surface*.—Both surfaces glabrous, upper side glossy, lower side matte.

*Petal margins*.—Entire, overlapping, medium amount of incisions, undulation weak to medium.

*Petal apex*.—Obtuse.

*Petal size*.—Average of 8 cm in length and 9 cm in width.

*Petaloids*.—Not present.

*Sepal number*.—5.

*Sepal shape*.—Ovate.

*Sepal margin*.—Entire.

*Sepal size*.—Average of 3.2 cm in length and 2 cm in width.

*Sepal aspect*.—Rotate, partly fused.

*Sepal surface*.—Both surfaces glabrous and matte.

*Sepal apex*.—Acute.

*Sepal base*.—Broadly cuneate and fused.

*Sepal color*.—Upper surface; 143B, flushed with 183A, lower surface 144B to 144C.

*Calyx*.—Rotate in shape, average of 5.6 cm in width, 3.2 cm in diameter.

*Pedicels*.—None.

*Peduncles*.—Average of 8 mm in length, 3 mm in width, glabrous surface, moderately strong, 144B in color.

*Epicalyx*.—Comprised of an average of 13 bracteoles, linear in shape, average of 3.4 cm in diameter, 1.5 cm in depth, 144B.

Reproductive organs:

*Gynoecium*.—1 pistil, average of 5 cm in length, stigmas; club-shaped, an average of 5 and 3A in color, style; 4 cm in length, 155A in color, ovary; 145B in color.

*Androecium*.—Stamens; average of 90, clustered and implanted in style, anthers; dorsifixed and orbicular in shape, 1 mm in length and 196B in color; filaments; 1 mm in length and 196B in color, pollen; moderate in quantity and 12B in color.

*Fruit/seeds*.—None observed to date.

It is claimed:

1. A new and distinct cultivar of *Hibiscus* plant named 'Tahi2025' as herein illustrated and described.

* * * * *